US00PP23200P2

(12) United States Plant Patent
Kobayashi

(10) Patent No.: US PP23,200 P2
(45) Date of Patent: Nov. 20, 2012

(54) POINSETTIA PLANT NAMED 'PER1230'

(50) Latin Name: ***Euphorbia pulcherrima* Willd.**
Varietal Denomination: PER1230

(75) Inventor: Ruth Kobayashi, Carlsbad, CA (US)

(73) Assignee: The Paul Ecke Ranch, Encinitas, CA (US)

( * ) Notice: Subject to any disclaimer, the term of this patent is extended or adjusted under 35 U.S.C. 154(b) by 28 days.

(21) Appl. No.: 13/065,259

(22) Filed: Mar. 17, 2011

(51) Int. Cl.
*A01H 5/00* (2006.01)

(52) U.S. Cl. ..... Plt./307; Plt./303

(58) Field of Classification Search ..... Plt./303, Plt./307
See application file for complete search history.

*Primary Examiner* — Susan McCormick Ewoldt
(74) *Attorney, Agent, or Firm* — C. A. Whealy

(57) ABSTRACT

A new and distinct cultivar of Poinsettia plant named 'PER1230', characterized by its uniform, upright and mounded plant habit; vigorous growth habit; freely branching habit; dark green-colored leaves; mid-season flowering response; large inflorescences with scarlet red-colored flower bracts; and good post-production longevity.

1 Drawing Sheet

Botanical designation: *Euphorbia pulcherrima* Willd.
Cultivar denomination: 'PER1230'.

BACKGROUND OF THE INVENTION

The present invention relates to a new and distinct cultivar of Poinsettia plant, botanically known as *Euphorbia pulcherrima* Willd., and hereinafter referred to by the name 'PER1230'.

The new Poinsettia plant is a product of a planned breeding program conducted by the Inventor in Encinitas, Calif. The objective of the breeding program is to create new uniform Poinsettia plants having large inflorescences with red-colored flower bracts, mid-season flowering habit and excellent post-production longevity.

The new Poinsettia plant originated from a cross-pollination made by the Inventor in December, 2004 of a proprietary selection of *Euphorbia pulcherrima* Willd. identified as code number 04-2816, not patented, as the female, or seed, parent, with *Euphorbia pulcherrima* Willd. 'PER1090', disclosed in U.S. Plant Pat. No. 18,203, as the male, or pollen, parent. The new Poinsettia plant was discovered and selected by the Inventor as a single flowering plant within the progeny of the stated cross-pollination in a controlled greenhouse environment in Encinitas, Calif. on Dec. 10, 2005.

Asexual reproduction of the new Poinsettia plant by terminal vegetative cuttings in a controlled greenhouse environment in Encinitas, Calif. since January, 2006 has shown that the unique features of this new Poinsettia plant are stable and reproduced true to type in successive generations of asexual reproduction.

SUMMARY OF THE INVENTION

Plants of the new Poinsettia have not been observed under all possible environmental conditions and cultural practices. The phenotype may vary somewhat with variations in environment such as temperature, daylength and light intensity, without, however, any variance in genotype.

The following traits have been repeatedly observed and are determined to be the unique characteristics of 'PER1230'.

These characteristics in combination distinguish 'PER1230' as a new and distinct Poinsettia plant:

1. Uniform, upright and mounded plant habit.
2. Vigorous growth habit.
3. Freely branching habit.
4. Dark green-colored leaves.
5. Mid-season flowering response; under natural season conditions, plants flower in late November in Southern California.
6. Large inflorescences with scarlet red-colored flower bracts.
7. Good post-production longevity.

In side-by-side comparisons conducted in Encinitas, Calif., plants of the new Poinsettia differ primarily from plants of the female parent in flower bract color and response time.

In side-by-side comparisons conducted in Encinitas, Calif., plants of the new Poinsettia differ primarily from plants of the male parent. 'PER1090' in the following characteristics:

1. Plants of the new Poinsettia are not as vigorous as plants of 'PER1090'.
2. Leaves and flower bracts of plants of the new Poinsettia are more lobed than leaves and flower bracts of 'PER1090'.
3. Flower bracts of plants of the new Poinsettia are scarlet red in color whereas flower bracts of plants of 'PER1090' are bright red in color.

Plants of the new Poinsettia can be compared to plants of the *Euphorbia pulcherrima* Willd. 'Peterstar', disclosed in U.S. Plant Pat. No. 8,259. In side-by-side comparisons conducted in Encinitas, Calif., plants of the new Poinsettia differed primarily from plants of 'Peterstar' in the following characteristics:

1. Plants of the new Poinsettia had darker green-colored leaves than plants of 'Peterstar'.
2. Flower bracts of plants of the new Poinsettia were scarlet red in color whereas flower bracts of plants of 'Peterstar' were bright red in color.

Plants of the new Poinsettia can also be compared to plants of the *Euphorbia pulcherrima* Willd. '490', disclosed in U.S.

Plant Pat. No. 7,825. In side-by-side comparisons conducted in Encinitas, Calif., plants of the new Poinsettia differed primarily from plants of '490' in the following characteristics:

1. Plants of the new Poinsettia flowered about one week later than plants of '490'.
2. Flower bracts of plants of the new Poinsettia were scarlet red in color whereas flower bracts of plants of '490' were dark red in color.

BRIEF DESCRIPTION OF THE PHOTOGRAPHS

The accompanying photographs illustrate the overall appearance of the new Poinsettia plant showing the colors as true as it is reasonably possible to obtain in colored reproductions of this type. Colors in the photographs may differ slightly from the color values cited in the detailed botanical description which accurately describe the colors of the new Poinsettia plant.

The photograph at the bottom of the sheet comprises a side perspective view of a typical flowering plant of 'PER1230' grown in a container.

The photograph at the top of the sheet is a close-up view of a typical inflorescence of 'PER1230'.

DETAILED BOTANICAL DESCRIPTION

Plants used in the aforementioned photographs and in the following description were grown during the winter in 16.5-cm containers in a polyethylene-covered greenhouse in Encinitas, Calif. and under natural season conditions and cultural practices which approximate those generally used in commercial Poinsettia production. During the production of the plants, day temperatures ranged from 20° C. to 27° C., night ranged from 15° C. to 20° C. and light levels ranged from 3,000 to 4,000 foot-candles. Measurements and numerical values represent averages for typical flowering plants. Plants were pinched one time and were 19 weeks old when the photographs and the description were taken. In the following description, color references are made to The Royal Horticultural Society Colour Chart, 2007 Edition, except where general terms of ordinary dictionary significance are used.

Botanical classification: *Euphorbia pulcherrima* Willd. 'PER1230'.

Parentage:

*Female, or seed, parent*.—Proprietary selection of *Euphorbia pulcherrima* Willd. identified as code number 04-2816, not patented.

*Male, or pollen, parent*.—*Euphorbia pulcherrima* Willd. 'PER1090', disclosed in U.S. Plant Pat. No. 18,203.

Propagation:

*Type*.—Terminal vegetative cuttings.

*Time to initiate roots*.—About seven to ten days at 20° C. night temperature and 27° C. day temperature.

*Time to produce a rooted young plant*.—About four weeks at 20° C. night temperature and 27° C. day temperature.

*Root description*.—Fibrous; white in color.

Plant description:

*Plant habit and form*.—Uniform, upright and mounded plant habit; inverted triangle; large inflorescences positioned above the foliar plane; vigorous growth habit.

*Plant height*.—About 32 cm.

*Plant diameter or spread*.—About 45 cm.

*Lateral branch description*.—Quantity: Freely branching habit, about ten lateral branches develop after pinching. Length: About 30 cm. Diameter: About 6 mm. Internode length: About 2.4 cm. Strength: Strong. Texture: Smooth, glabrous. Color: Close to 146B.

*Foliage description*.—Arrangement: Alternate, simple. Aspect: Flat. Length: About 14.2 cm. Width: About 9 cm. Shape: Ovate with shallow lobes. Apex: Acuminate. Base: Attenuate. Margin: Entire with shallow lobes. Venation pattern: Pinnate, arcuate. Texture, upper surface: Sparsely pubescent. Texture, lower surface: Pubescent. Color: Developing leaves, upper surface: Close to 139A. Developing leaves, lower surface: Close to 137B. Fully expanded leaves, upper surface: Darker than N189A; venation, close to 191A. Fully expanded leaves, lower surface: Close to N137A; venation, close to 147C. Petiole: Length: About 7.2 cm. Diameter: About 3 mm. Texture, upper and lower surfaces: Smooth, glabrous. Color, upper surface: Close to 187B. Color, lower surface: Close to 183B.

Inflorescence description:

*Inflorescence type and habit*.—Inflorescences are compound corymbs of cyathia with colored flower bracts subtending the cyathia; inflorescences positioned above the foliar plane.

*Quantity of inflorescence*.—One inflorescence develops per lateral branch.

*Fragrance*.—Not detected.

*Flowering response*.—Mid-season flowering response; under natural season conditions, plants typically flower on November 25$^{th}$ in Southern California; under artificial long nyctoperiod/short photoperiod conditions, plants flower about 8.5 weeks later.

*Post-production longevity*.—Good post-production longevity; plants of the new Poinsettia maintain good substance and flower bract color for about four weeks under interior conditions; inflorescences persistent.

*Inflorescence size*.—Diameter: About 30 cm. Height (depth): About 8 cm to 9 cm.

*Flower bracts*.—Quantity per inflorescence: About 23. Length, largest bracts: About 14.4 cm. Width, largest bracts: About 11.4 cm. Shape: Ovate to elliptical with shallow lobes. Apex: Acuminate. Base: Attenuate. Margin: Entire or with shallow lobes. Texture, upper and lower surfaces: Smooth, glabrous. Aspect: Mostly horizontal. Venation pattern: Pinnate, arcuate. Color: Developing or transitional bracts, upper surface: Close to 53B to 53C. Developing or transitional bracts, lower surface: Close to 180B. Fully expanded bracts, upper surface: Close to 45A; venation, close to 45A; color becoming closer to 46B with development. Fully expanded bracts, lower surface: Close to 46C; venation, close to 46C; color becoming closer to 47A with development. Bract petiole: Length: About 3.7 cm. Diameter: About 2 mm. Texture, upper and lower surfaces: Smooth, glabrous. Color, upper and lower surfaces: Close to 183B.

*Cyathia*.—Quantity per corymb: About 12 to 15. Length: About 1 cm. Width: About 5 mm. Shape: Ovoid. Color, immature: Close to 144A. Color, mature: Close to 146B.

*Nectaries*.—Quantity per cyathium: One. Length: About 4 mm. Width: About 2.5 mm. Shape: Elliptical to ovoid. Color: Close to 21A.

*Peduncles*.—Length: About 6 mm. Diameter: About 4 mm. Strength: Strong. Aspect: Mostly upright. Texture: Smooth, glabrous. Color: Close to 146C.

*Reproductive organs*.—Stamens: Quantity per cyathium: About ten to twelve. Filament length: About 3 mm. Filament color: Close to 53A. Anther shape: Oval; bi-lobed. Anther length: About 1 mm. Anther color: Close to 187B. Amount of pollen: Scarce. Pollen color: Close to 13A. Pistils: Plants of the new Poinsettia have not been observed to develop pistils. Seed/fruit: Seed and fruit production has not been observed.

Disease/pest resistance: Plants of the new Poinsettia have not been shown to be resistant to pathogens and pests common to Poinsettias.

Temperature tolerance: Plants of the new Poinsettia have been observed to tolerate temperatures ranging from about 15° C. to about 35° C.

It is claimed:

1. A new and distinct Poinsettia plant named 'PER1230' as illustrated and described.

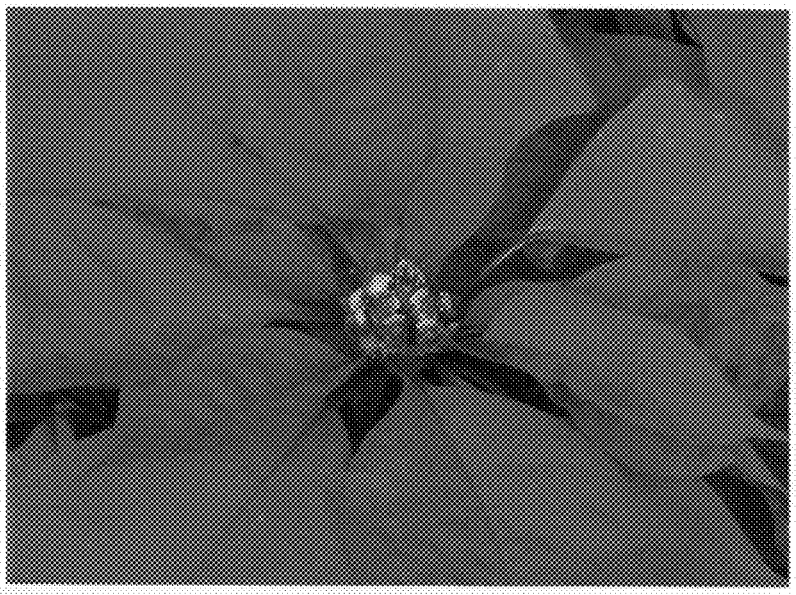
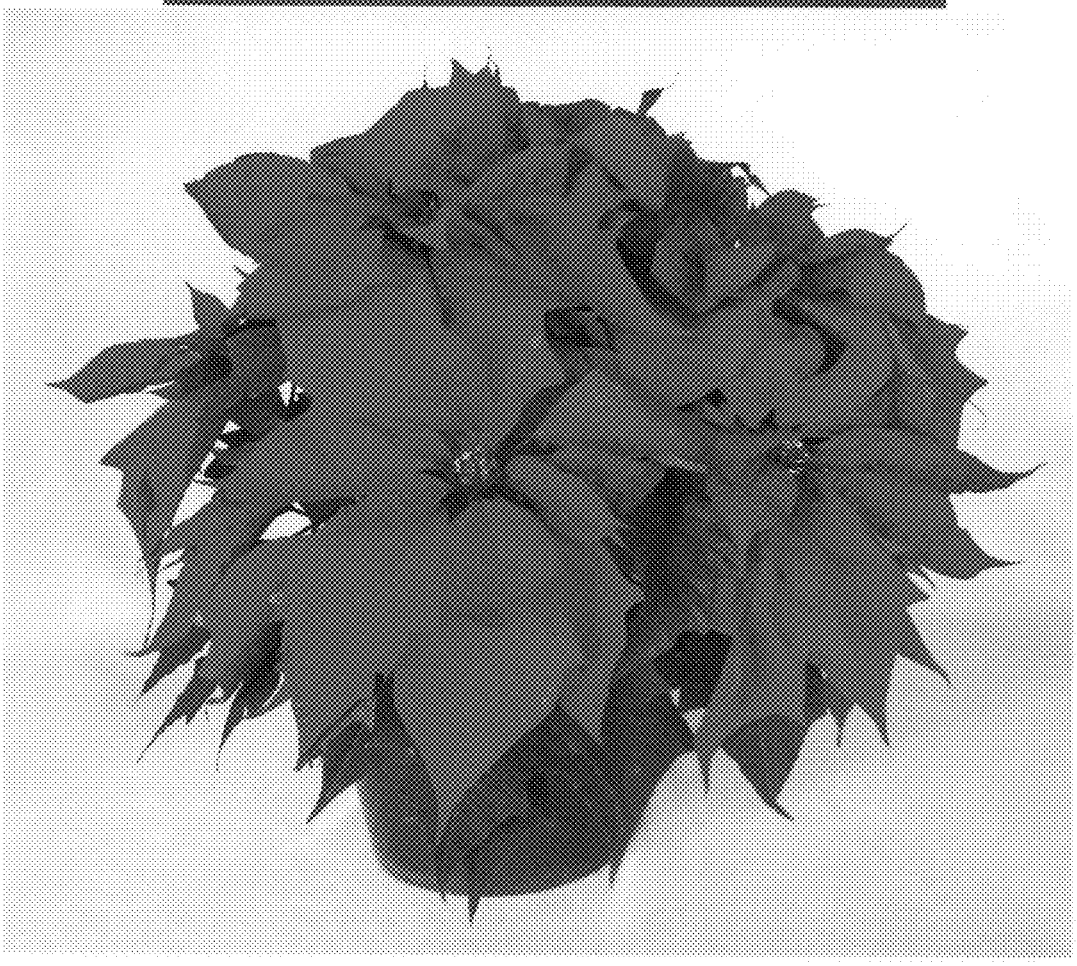

* * * * *